United States Patent
Thompson et al.

(10) Patent No.: US 8,888,289 B2
(45) Date of Patent: Nov. 18, 2014

(54) REFRACTOMETER WITH A REMOTE WAVEFRONT GENERATOR

(71) Applicant: DigitalVision, LLC, Atlanta, GA (US)

(72) Inventors: Keith P. Thompson, Atlanta, GA (US); Jose R. Garcia, Mableton, GA (US)

(73) Assignee: DigitalVision, LLC, Atlanta, GA (US)

( * ) Notice: Subject to any disclaimer, the term of this patent is extended or adjusted under 35 U.S.C. 154(b) by 0 days.

(21) Appl. No.: 13/738,644

(22) Filed: Jan. 10, 2013

(65) Prior Publication Data

US 2013/0176537 A1    Jul. 11, 2013

Related U.S. Application Data

(60) Provisional application No. 61/585,096, filed on Jan. 10, 2012.

(51) Int. Cl.
*A61B 3/02* (2006.01)
*A61B 3/00* (2006.01)

(52) U.S. Cl.
USPC .......................................... 351/239; 351/246

(58) Field of Classification Search
USPC .................................................. 351/200–246
See application file for complete search history.

(56) References Cited

U.S. PATENT DOCUMENTS

| | | | |
|---|---|---|---|
| 3,305,294 A | 2/1967 | Alvarez |
| 3,860,330 A | 1/1975 | Persson |
| 3,874,774 A | 4/1975 | Humphrey |
| 4,015,899 A | 4/1977 | Humphrey |
| 4,043,644 A | 8/1977 | Humphrey |
| 4,385,813 A | 5/1983 | Klein et al. |
| 4,523,822 A | 6/1985 | Thurston |
| 4,820,040 A | 4/1989 | Sims |
| 6,688,745 B2 | 2/2004 | Ross et al. |
| 6,709,108 B2 | 3/2004 | Levine et al. |
| 6,722,767 B2 | 4/2004 | Dick et al. |
| 6,827,442 B2 | 12/2004 | Ross et al. |
| 6,932,475 B2 | 8/2005 | Molebny et al. |
| 6,964,480 B2 | 11/2005 | Levine |
| 6,997,555 B2 | 2/2006 | Dick et al. |
| 7,195,354 B2 | 3/2007 | Olivier et al. |
| 7,387,387 B2 | 6/2008 | Dai |
| 7,553,022 B2 | 6/2009 | Neal et al. |
| 7,654,672 B2 | 2/2010 | Zhao et al. |
| 7,703,919 B2 | 4/2010 | Thompson et al. |

(Continued)

OTHER PUBLICATIONS

International Search Report for PCT/US2013/021025.

(Continued)

*Primary Examiner* — Mohammed Hasan
(74) *Attorney, Agent, or Firm* — McClure, Qualey & Rodack, LLP (57) ABSTRACT

A vision testing method and apparatus are disclosed, the method including generating an image, modulating the wavefront of the image remote from the patient, relaying the modulated wavefront to a plane nearby, on, or within the patient's eye, varying the modulation of the wavefront based upon patient or operator response, and conveying the value of the wavefront modulation to the operator. The apparatus includes devices for generating an image, modulating the wavefront of the image that is physically remote from the patient, optically relaying the modulated wavefront of the image to a plane nearby, on, or within a patient's eye, varying the modulation of the wavefront of the image based upon patient or operator response, and conveying the value of the continuously modulated wavefront to the operator.

24 Claims, 6 Drawing Sheets

(56) References Cited

U.S. PATENT DOCUMENTS

| | | | |
|---|---|---|---|
| 7,708,410 B2 * | 5/2010 | Dai | 351/239 |
| 7,815,310 B2 | 10/2010 | Su et al. | |
| 7,909,463 B2 | 3/2011 | Dick et al. | |
| 7,926,944 B2 | 4/2011 | Thompson et al. | |
| 8,083,353 B2 * | 12/2011 | Hytowitz | 351/239 |
| 8,118,427 B2 | 2/2012 | Bonnin et al. | |
| 8,562,136 B2 * | 10/2013 | Blixt et al. | 351/210 |
| 2002/0140902 A1 | 10/2002 | Guirao et al. | |
| 2009/0153803 A1 | 6/2009 | Frisen | |
| 2010/0265463 A1 | 10/2010 | Lai | |
| 2011/0205491 A1 | 8/2011 | Koiwa et al. | |
| 2011/0228226 A1 | 9/2011 | Pixton et al. | |

OTHER PUBLICATIONS

Lateral-shift variable aberration generators, Iwona A. Palusinski, Jose' M. Sasia' n, and John E. Greivenkamp; Applied Optics y vol. 38, No. 1 y Jan. 1, 1999.

Development of variable-focus lenses and a new refractor. Luis W. Alvarez, PhD, ScD, Jan. 1, 1987.

* cited by examiner

| No. | Lens Element |
|---|---|
| 29 | Accessory |
| 30 | Accessory |
| 31 | Spherical Aberration Element A |
| 32 | Spherical Aberration Element B |
| 33 | Comatic Element A |
| 34 | Comatic Element B |
| 35 | 0°-90° Jackson Cross Cylinder Element A |
| 36 | 0°-90° Jackson Cross Cylinder Element B |
| 37 | 45°-135° Jackson Cross Cylinder Element A |
| 38 | 45°-135° Jackson Cross Cylinder Element B |
| 39 | Spherical Element A |
| 40 | Spherical Element B |
| 41 | Accessory |
| 42 | Accessory |
| 43 | Accessory |
| 44 | Accessory |
| 45 | Accessory |

REFRACTOMETER WITH A REMOTE WAVEFRONT GENERATOR

FIELD OF INVENTION

This invention relates to subjective, binocular, patient-interactive vision testing.

DESCRIPTION OF THE PRIOR ART

The phoropter lens dial such as the one described in U.S. Pat. No. 4,523,822 is the most common vision testing device in present use. The phoropter is comprised of dials of lenses of fixed spherical and cylindrical power that vary in 0.25 D or 0.125 D increments. During vision testing, the phoropter is placed in front of the patient's eyes and different lenses are dialed into the device's viewing aperture while the patient views letters on an eye chart through the selected lenses. Based upon an increase or decrease in image clarity perceived by the patient with each lens combination, the refractionist iteratively determines the best combination of spherical and cylindrical lenses that corrects eyesight and then records these values as the eyeglass prescription. It is known to those skilled in the art that conventional eyeglass prescriptions are provided in dioptric power, "D" (a lens with −F1 Diopter of optical power focuses parallel light at 1 meter) in increments of 0.25 D or 0.125 D resolution ($\frac{1}{4}^{th}$ or $\frac{1}{8}^{th}$ diopter).

To those skilled in the art, the phoropter has known deficiencies that include a measurement resolution that is limited by the differences in power of its fixed power lenses, the propensity to induce instrument accommodation, a limited field of view, and examination tasks that some patients find ambiguous.

In U.S. Pat. No. 3,305,294, Alvarez described a two-element lens system capable of adjustable optical power. The Alvarez lens was comprised of paired lens elements, each with a surface shape defined by a cubic polynomial equation. When one element of the Alvarez lens pair was translated in a direction perpendicular to its optical axis, the optical power of the lens pair varied with the amount of translation.

U.S. Pat. No. 3,874,774 to Humphrey described a subjective, binocular vision testing instrument referred to herein as the Humphrey Vision Analyzer ("HVA"). Rather than use lenses of fixed power, the HVA incorporated a single pair of variable power Alvarez lenses to provide spherical corrections and a second and third pair of Alvarez lenses, arranged in series along the optical axis of the instrument to provide variable astigmatic corrective power along the 0°-90° and the 45°-135° axis, respectively. The use of two Alvarez cylindrical lenses of fixed axes and variable power was used to generate a resultant cylindrical power at any desired axis in 0.125 D or 0.25 D increments. The use of variable power Alvarez lenses in the HVA refractometer was an inventive feature over the lenses of fixed power in the phoropter and in similar prior art devices.

In the phoropter and similar prior art methods, corrective lenses are physically placed immediately in front of the patient. In the HVA, the lenses were located remotely in a cabinet that was interposed between the patient and the operator and the optical properties of the Alvarez lenses were imaged—or optically relayed—to the appropriate plane near the patient's eye by a concave field mirror located approximately 3 Meters in front of the patient. Humphrey referred to this arrangement as a "phantom lens architecture" and it eliminated the placement of a bulky apparatus near the patient's eyes. When viewing images in the HVA field mirror, it appeared to the patient as if invisible "phantom" corrective lenses were placed before his eyes and it permitted vision testing to be conducted under natural viewing conditions without the inducement of instrument accommodation, a common source of error inherent with the phoropter and similar prior art devices.

Since the U.S. Pat. No. 3,874,774 patent was issued in 1975, improvements in lens manufacturing technology now permit spectacle lenses to be fabricated to resolutions of 0.01 D, or less, approximately ten-fold greater resolution than the 0.125 D and 0.25 D resolutions provided by the phoropter, the HVA, and other prior art vision testing methods. Similar resolutions can now be attained in contact lens fabrication and by laser vision treatment with LASIK and PRK surgery.

Aberrometers, wavefront sensors, and spatially resolved refractometers have also recently become available to measure the higher order aberrations of the eye such as spherical aberration, coma, and trefoil. Incorporating aberrometry measurements into the designs of various optical corrections may provide patients with better vision, enhanced wearing comfort, and improved depth of field than corrections that are based only upon the conventional ophthalmological measures of sphere and cylindrical lenses that have resolution limited to 0.125 D or 0.25 D.

U.S. Pat. Nos. 7,703,919B2 and 7,926,944B have been issued for a new method of measuring vision based upon the neuro-ocular wavefront error, a metric that the inventors claim to be more accurate than conventional ophthalmic prescriptions or ocular aberrometry measurements.

Although the Humphrey Vision Analyzer had improved features over prior art binocular vision testing devices, the HVA's dioptric resolution was no better than that of the phoropter because the devices adjustable lenses were used to emulate an ophthalmological prescription and the maximum measurement resolution of the device was 0.125 D. The HVA had no capability to obtain new visual metrics such as higher order aberrations or the neuro-ocular wavefront error. Stated differently, the HVA could not modulate the wavefront of the image except in a fixed sphero-cylindrical fashion in minimum increments of 0.125 D In the HVA the patient viewed the image in the field mirror at an angle that was offset 10° in the vertical direction. This off-axis viewing angle induced both unwanted astigmatism and higher order aberrations. In an attempt to compensate for the induced astigmatism, Humphrey taught the fabrication of a spherical mirror and then deformed the mirror into a toroidal shape with a mechanical clamp described in U.S. Pat. No. 4,043,644. However, once installed in the doctor's office, there was no assurance that the mirror maintained the required shape over time. Higher order aberrations caused by off-axis viewing and/or by the distortion of the mirror shape were neither detected nor corrected in the HVA device. These deficiencies limited the optical performance and accuracy of the device and the refractive measurements made by the HVA and thereby degraded the performance of the corrective eyewear that was prescribed using its measurements.

Another limitation of the U.S. Pat. No. 3,874,774 invention was the complicated method required to set the HVA to a desired corrective power. The operator was required to first dial one control wheel to set the spherical power and then to dial two different wheels in order to set the desired astigmatic power and axis. Because the astigmatic correction was the resultant vector sum of the power of the two Alvarez cylindrical lenses, each of which was controlled by a different dial, setting the power and axis of astigmatism was a difficult and non-intuitive task for the operator, especially for those trained in the use of the phoropter where a single knob controlled the axis of the cylindrical power and a second knob controlled the cylindrical power.

The HVA optics were housed in a bulky desk that was interposed between the patient and the examiner that occupied a significant portion of the exam room space. The desk interfered with the doctor's access to the patient and precluded him from using the slit lamp microscope and indirect ophthalmoscope, instruments necessary for conducting eye health exams. This caused a delay in workflow and inconvenience to the patient.

To overcome these and other limitation with the U.S. Pat. No. 3,874,774 device a novel method and apparatus for vision testing is described herein.

SUMMARY

A vision testing method is disclosed comprised of generating an image, modulating the wavefront of the image remote from the patient, relaying the modulated wavefront to a plane nearby, on, or within the patient's eye, varying the modulation of the wavefront based upon patient or operator response, and conveying the value of the wavefront modulation to the operator.

A vision testing apparatus is disclosed providing a means of generating an image, a means of modulating the wavefront of the image, said modulating means physically remote from the patient, means of optically relaying the modulated wavefront of the image to a plane nearby, on, or within the patient's eye, means of varying the modulation of the wavefront of the image based upon patient or operator response, and means of conveying the value of the continuously modulated wavefront to the operator

DETAILED DESCRIPTION

Figure 1:
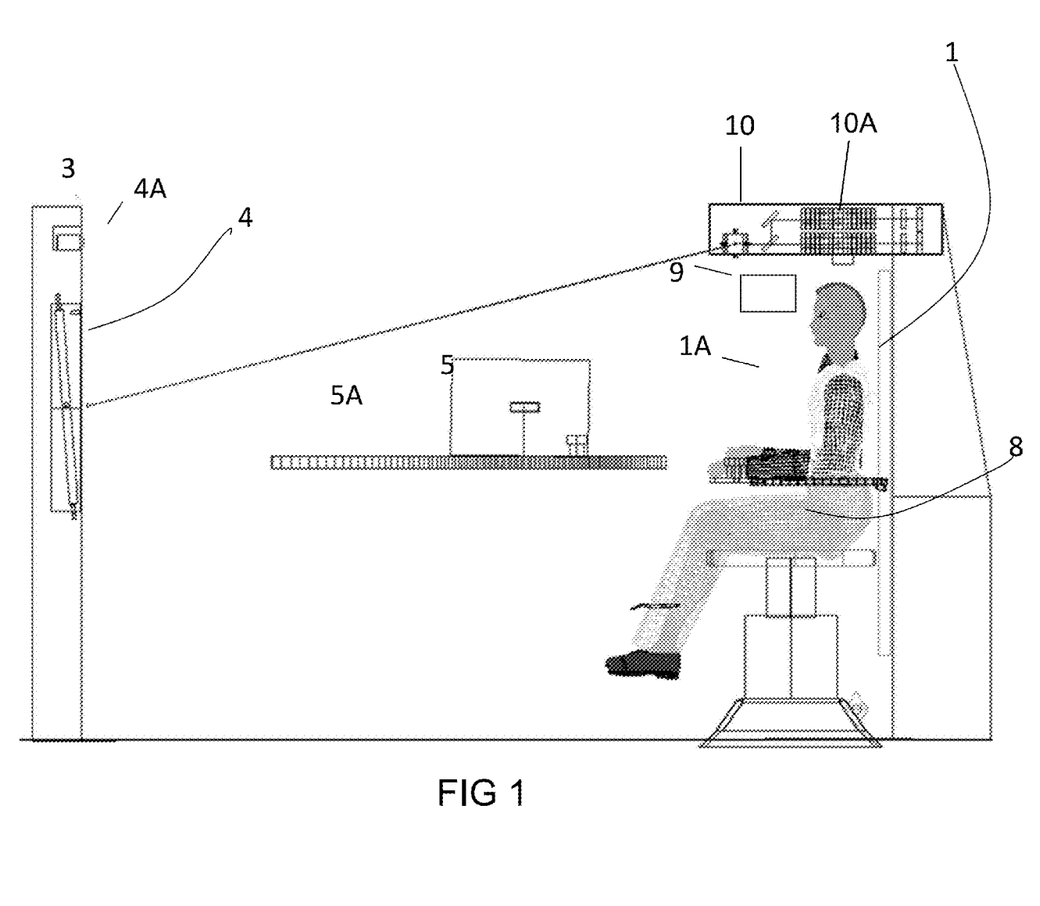
FIG. 1 is a diagrammatical side elevational view of the apparatus with patient seated in the exam chair
Figure 2:
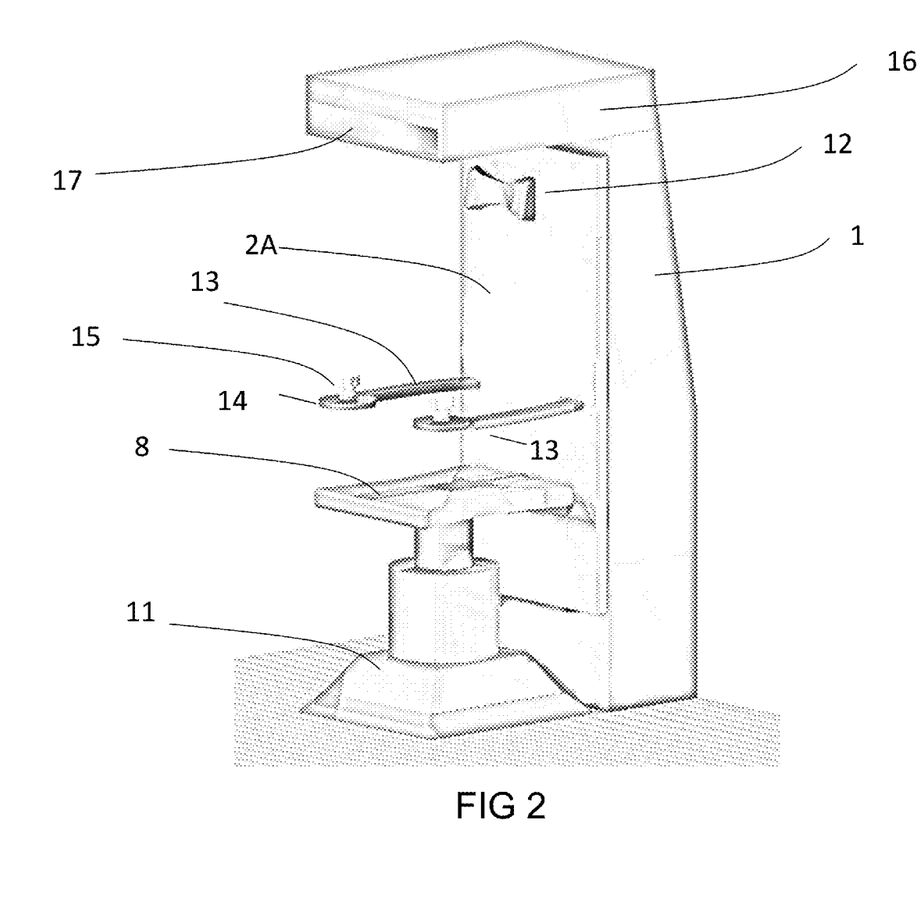
FIG. 2 is a perspective view of the patient chair and rear tower

In general, the present apparatus is intended to be deployed in the examination lane of eye care professionals with typical dimensions of 8'×10.' As shown in FIGS. 1 and 2, the apparatus consists of tower 1, an examination chair 2A, a viewport 3 which houses a reflective field mirror 4 and one or more optional cameras 4A, and an operator control terminal 5. The patient 1A undergoing vision testing with the apparatus is seated in the examination chair seat 8 which is adjusted to place the patient's eyes within the desired examination position noted by box 9. Images are generated by wavefront generators 10A or other means in the optical tray 10 and directed to a field mirror 4 in the viewport 3 where they are reflected to the patient's eyes located within the desired examination position 9. Behind the patient, rear cabinet 1 houses a computer, power supply, and other specialty electronics to control the wavefront generators, located in optical tray 10. Images projected from the optical tray are reflected by field mirror 4 and viewed by the patient.

FIG. 2 shows a perspective view of the examination chair 2A that is located adjacent, and forward of, the vertical tower 1, and it is preferentially mechanically isolated from the tower 1 so that patient movements in the chair are isolated from the optical components in the tower. The examination chair has a seat portion 8, the position of which is adjustable through motor means located in the base of the chair 11 that may be made responsive to the system computer. The seat back has a head rest 12 that may be adjustable through manual or by automatic means made responsive to the System computer. Optional head restraint (not shown) may be deployed from the underside of optical tray 10 to aid in stabilizing the patient during the exam.

The examination chair has arm rests 13, each of which has a platform 14 for supporting patient input means 15. In one preferred embodiment, the input means is a rotary haptic dial that the patient may rotate, translate, or depress to provide input to the system computer during the examination. Suitable haptic controllers are manufactured by Immersion Technologies, San Jose, Calif. 95131, and such controllers are particularly suited to providing intuitive input to the System during the exam. Numerous other input devices are known, such as a mouse, a joystick, a rotary control, touch-sensitive screen, voice, and other control means, any of which may be employed as alternative embodiments for use with the present apparatus.

Figure 3:
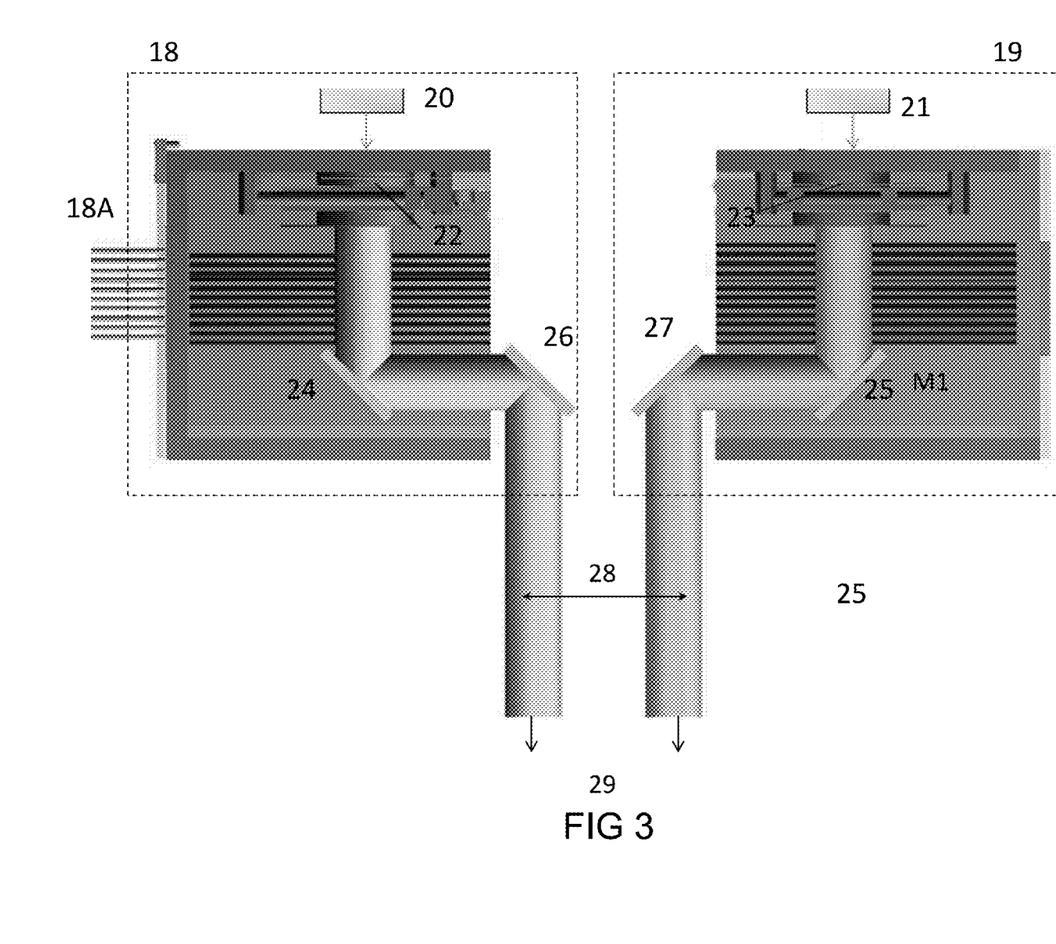
FIG. 3 is a partial top plan view of the wavefront generators for the right and left eyes with the adjustable lenses removed

FIG. 3 shows a top view of the wavefront generators for the right eye 18 and left eye 19 with the adjustable lenses and accessory lenses removed. Display means for the right eye 20 and left eye 21 generate images. One suitable image generating means is model SXGA OLED-XL™, made by EMagin Company, Bellevue, Wash. Numerous other image generating means and modalities are known in the art including LED, OLED, DLP, CRT and other means, any and all of which may be suitable for alternative embodiments for use with the present apparatus.

Images generated by 20 and 21 pass through collimating lenses 22 and 23. Collimated light of the images then traverses the stack of adjustable Alvarez lens elements and accessory lens elements, shown in detail in FIG. 4, and described below, where they are redirected by beam turning mirrors 24 and 26 for the right eye, and by turning mirrors 25 and 27 for the left eye where they are then directed towards the field mirror 29. The position and angle of lenses 24, 25, 26, and 27 are made responsive to the System computer in order to direct the beam to the field mirror and to adjust the spacing between the left and right beam paths to that of the patient's inter-pupillary distance, 28. Suitable adjustable lenses for the apparatus are lenses described by Alvarez in U.S. Pat. No. 3,305,294. These lenses consist of pairs of lens elements, each of which has a surface shape that can be described by a cubic polynomial and each element is a mirror image of its fellow element. As the lens elements are made to translate relative to each other in a direction that is perpendicular to the optical axis of the element, the optical power imparted to an image passing through them changes as a function of the amount of translation. The lenses are mounted in surrounding frames and they are translated by motion means 28 such that their movement is responsive to the system computer. The wavefront of the image is changed as it traverses each lens element. The total change imparted as the image exits the last optical element of the wavefront generator is referred to herein as the modulation of the wavefront of the image. Such modulation can also be effected by other suitable optical means known to those skilled in the art.

It is known to those skilled in the art that the co-efficients of the equations that define the shape of the Alvarez lens elements may be optimized to improve their optical performance, by, for example, using suitable optical design software such as ZeMax (Radiant ZEMAX LLC, 3001 112th Avenue NE, Suite 202, Bellevue, Wash. 98004-8017 USA). Such modifications of the adjustable lenses to improve their performance are fully envisioned within the scope of the present disclosure.

Other types of adjustable lenses and mirrors are known in the art that may be used in the wavefront generator to modulate the wavefront of the image and they are considered to be within the scope of the disclosure. Deformable mirrors that may be made responsive to a computer are known such as those manufactured by Edmunds Optics, 101 East Gloucester Pike, Barrington, N.J. 08007-1380. As one alternative embodiment, the adjustable Alvarez lenses described above may be replaced by fixed lenses, by one or more deformable mirrors, or by any combination of fixed lenses, deformable mirrors, and Alvarez lenses and remain under the scope of the disclosure. In another alternate embodiment, one or a plurality of discrete lenses, disposed in a rack or other arrangement, may be substituted in order to modulate the wavefront of the image.

Figure 4:
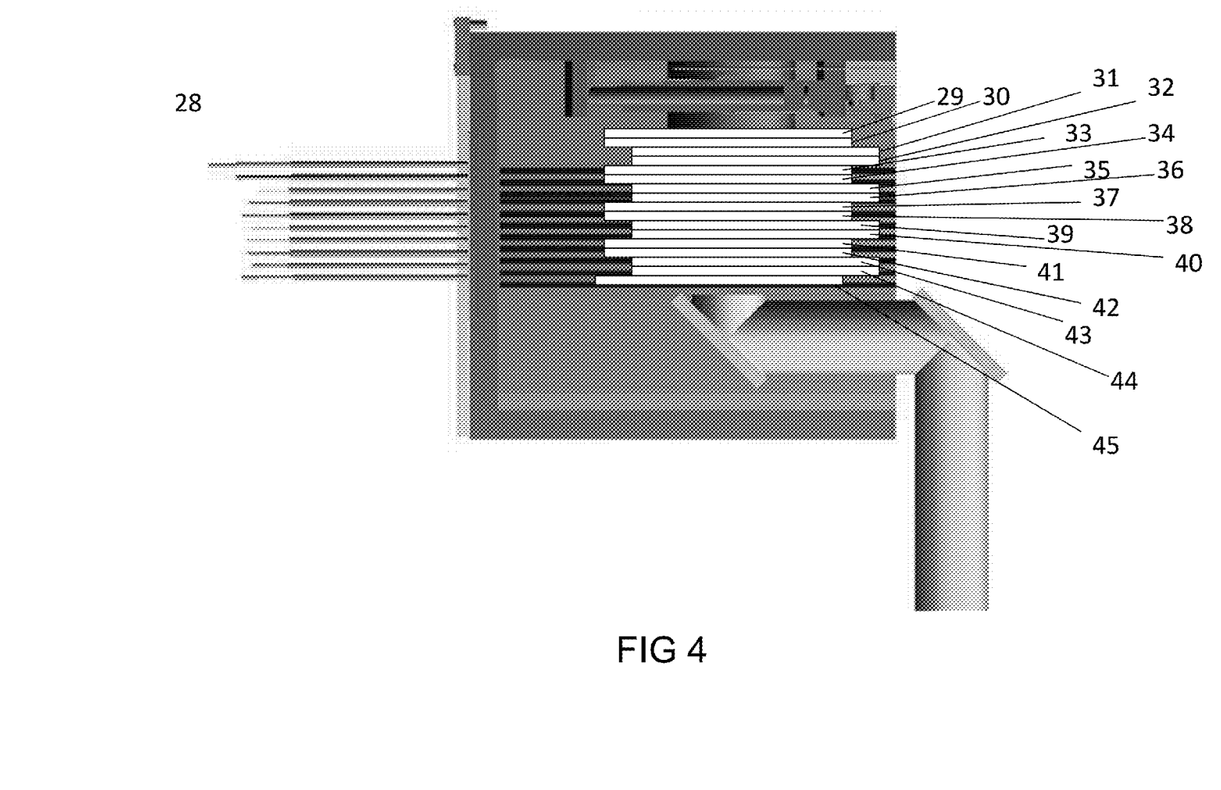
FIG. 4 is a partial detailed view of the wavefront generator for the right eye with the adjustable lenses in position

FIG. 4 shows a more detailed view of the wavefront generator for the right eye showing the adjustable Alvarez lens pairs and the accessory lens pairs 29-45 that are used to modify the wavefront of the image that is created by display means 20. The identity of these lenses is shown in FIG. 5.

In one preferred embodiment, the relationship between the linear separation of the Alvarez lens elements and the spherical modulation of the wavefront of the image has been found to be 2.1 mm=1 D, and for the linear separation of the Alvarez lens elements and the cylindrical modulation of the wavefront of the image has been found to be 1.8 mm=1 D.

A suitable magnetic or optical position encoder (such as provided by Renishaw's Encoder Read Head T 1 0 0 1 15 A and Encoder Scale A-9420-0006M) may be placed on the bottom of lens elements 29-45 and a signal sent to the System computer for use in determining the location of the lens elements. Such means may be employed for calibration or for continuous operation purposes.

Figure 5:
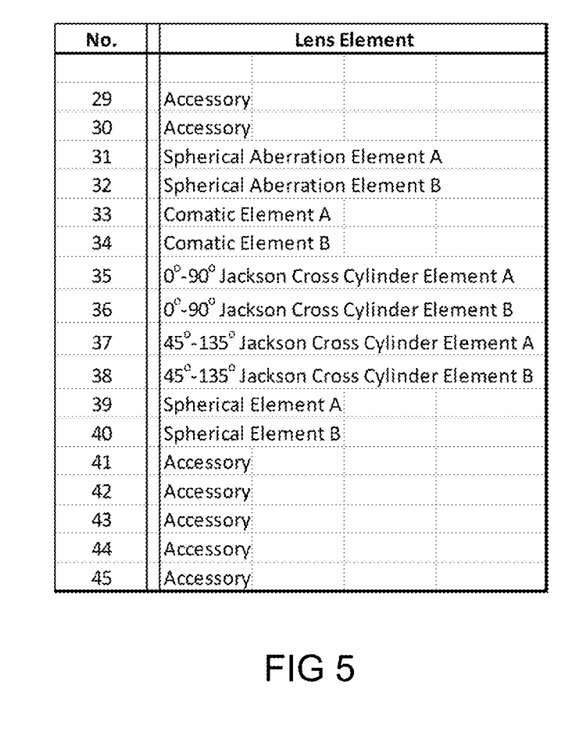
FIG. 5 is a table listing the identity of the adjustable lens elements shown in FIG. 4.

In general, it is envisioned that the optical elements listed in FIG. 5 will be selected to modulate the wavefront of the image to provide a full range of correction of sphero-cylindrical refractive errors from −20D to −F20 D and astigmatic corrections up to, or beyond, 8 D. The apparatus is capable of providing continuously adjustable wavefront modulation in any increment desired by the operator in ranges between 0.005 D to 20 D increments. This continuously adjustable wavefront modulation of variable resolution is a major improvement over the prior art HVA, the phoropter, and other prior art because high resolution steps (e.g. 0.01 D) can be selected to provide very fine wavefront modulations to achieve optimal vision and to create specifications for corrective eyewear at much higher resolution than conventional ophthalmological eyeglass prescriptions that are limited to 0.125 D and 0.25 D resolution. By providing this inventive feature, the present apparatus can provide specifications for corrective eyewear to a resolution that the new generation of spectacle lens fabrication technologies can now create accurately. Such variable resolution is also useful for the operator to set the apparatus to low resolution steps (e.g. 1.0 D) in certain situations such as examining patients with low vision in order to speed their vision exam.

In addition to modulating the spherical and cylindrical components of the wavefront of the image, the wavefront generator described herein is able to modulate the wavefront to achieve the correction of higher order aberrations such as spherical aberration by directing the motions of lens elements 31 and 32 and comatic aberrations by directing the motions of lens elements 33 and 34. As one alternative embodiment, the wavefront generator may utilize fixed and adjustable lens elements to modulate spherical and astigmatic errors and deformable mirror elements to modulate higher order aberrations of the wavefront of the image.

FIG. 1 shows a side view of the viewport 3, which houses the field mirror 4. In one preferred embodiment, the field mirror is round in shape and has a spherical concave curvature with a radius of curvature approximately 2.5M and a diameter between 10" and 24." Such mirrors are known in telescopic applications and a suitable mirror may be procured from Star Instruments, Newnan, Ga. 30263-7424. Alternative embodiments for spherical mirrors are known such as CFRP (carbon fiber reinforced polymer) spherical rectangular mirrors which may be procured from Composite Mirrors Applications in Arizona.

Alternative embodiments for the field mirror include the use of an aspheric mirror, a toroidal mirror, a mirror that is non-circular in shape, and a plano mirror.

In one preferred embodiment, the radius of curvature of the mirror corresponds to the approximate distance between the spectacle plane of the patient's eyes (at the nominal testing position 9) to the mirror, and from the center of the lenses in the wavefront generator to the field mirror. It is known to those skilled in the art that a real object placed at a distance that is twice the focal length (or at the radius of curvature) of a concave spherical mirror will produce a real inverted image of the object with a magnification of one, or "unity magnification." In this configuration, the object and image are said to occupy conjugate planes, a property of lenses and mirrors that is well known to those skilled in the art. Stated differently, it can be said that when the object and its image occupy conjugate planes, the optical properties of the object in the object plane are reproduced exactly by the image in the image plane as if the physical object itself was located in the image plane. It can also be said that the object has been optically relayed to the conjugate image plane.

An inventive feature of the U.S. Pat. No. 3,874,774 patent was the recognition that the optical relay property of concave mirrors could be applied to corrective optical lenses as well as physical objects. Specifically, Humphrey recognized that the corrective power of the adjustable Alvarez lenses located at a distance equal to the radius of curvature of the concave field mirror would be effectively relayed to a position equidistant from the concave mirror at the conjugate image plane. When the patient's spectacle plane was located at the center of curvature of the field mirror and the corrective adjustable lenses were the same distance away (albeit at a slightly different angle relative to the mirror), then the properties of the corrective adjustable lenses would be optically relayed to the patient's spectacle plane.

It will also be apparent to those skilled in the art that operating the apparatus at, or near a condition of "unity magnification" (i.e. when the correcting lenses and the patient's spectacle lenses are located a distance from the concave spherical field mirror a distance that is equal to the radius of curvature) is one preferred embodiment. However, it is known that changes in effective lens power that result from Alvarez lenses imaged at non-unity magnifications may be compensated for by the following equation:

$$Po = Pc(M)^2$$

Where Po is the effective power of the lens at the patient's spectacle plane, Pc is the power of the corrective lenses in the wavefront generator, and M is the magnification, given by Do/Di, where Do is the distance between the corrective lenses and the field mirror and Di is the distance between the field mirror and the patient's eyes. This relationship may be employed to adjust Po when the patient's eyes are at distances from the field mirror other than at the radius of curvature.

As shown in FIG. 1, a desk 5A is provided to support the display terminal 5 used by the operator to provide control inputs to the computer and to receive displays from the device. Operator input to the system may be provided by conventional keyboard, mouse, or optional haptic means 15 to control the apparatus during the examination. These devices are connected to the system computer through conventional cable, fiber optic, or wireless means. Other input means are known to those skilled in the art such as voice and gesture input and these and other inputs are considered to be within the scope of the disclosure.

Figure 6:
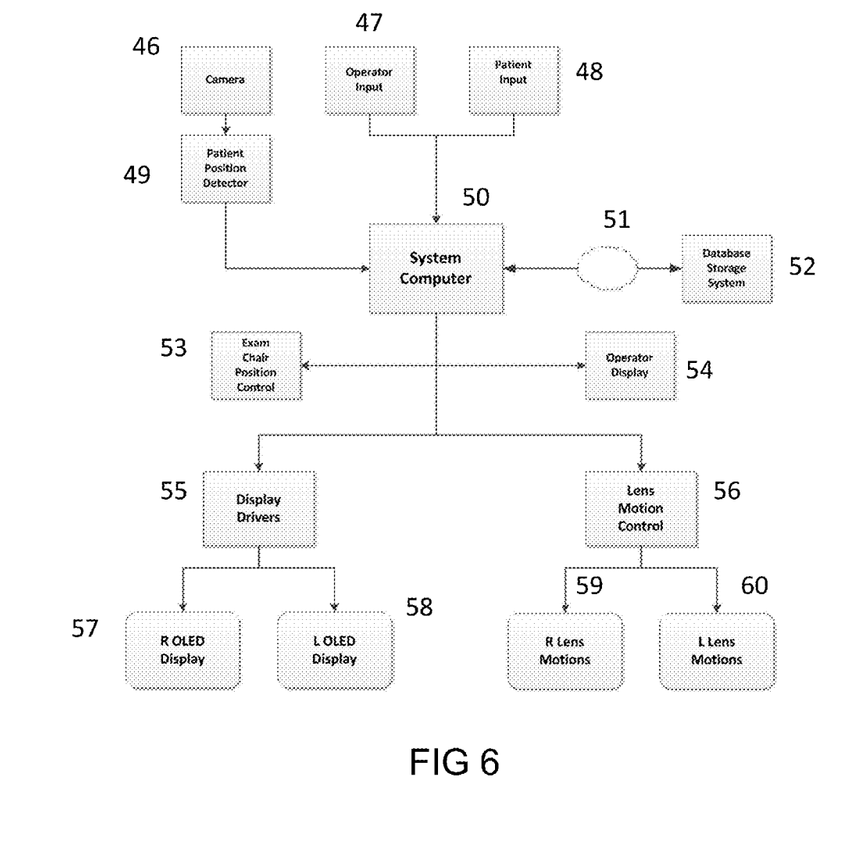
FIG. 6 is a block diagram of inputs and outputs of the System computer.

FIG. 6 shows inputs and outputs of the system computer 50 to different subsystems of the apparatus. Camera 46 provides information to the patient position detector 49, which provides input to system computer 50. Operator inputs 47 and patient inputs 48 are provided to the system computer.

The system computer 50 receives inputs and provides outputs to database storage system 52, which in one preferred embodiment may be transmitted through the Internet 51.

The system computer 50 provides outputs to display drivers 55 which run the digital displays 57 and 58 which, in one preferred embodiment, may be organic light emitting diodes described above. The system computer 50 provides outputs to lens motion control system 56 which directs the actuators that drive the adjustable lenses for the right and left channels of the wavefront generators, 59 and 60, respectively.

In one preferred embodiment, information from one or more cameras 4A can be sent to an appropriate eye tracking software such as (SmartEye created by Smart Eye AB in Gothenburg, Sweden; Tobbi created by Tobii Technology AB in Danderyd, SWEDEN; or faceLAB from Seeing Machines Inc in Tucson, Ariz.) to determine the distance between the patient's eyes and the viewport mirror. Once this distance is known, the formula listed above can be used to calculate the effective power of the lens at the patient's actual position. Such a feature allows the patient to move freely within a defined range 9 while the system automatically calculates the correction to be applied to the effective power of the lenses in the wavefront generator. This is one significant inventive feature over the prior art, as it allows the patient to test under natural viewing conditions and be free to move about without the need to be restrained by a forehead or head rest. It also improves the accuracy of the measurements by ensuring that the proper calibration factor is applied based upon the actual position of the patient.

This formula can provide corrective conversions through calibration tables and/or by adjusting the lenses in the Alvarez stack 25A to correct for the operation of the device at such non-unity magnifications. Such corrections may be made by the system computer automatically without input by the operator. It is also known that only one location in the Alvarez stack can be at the center of curvature, and that correction factors must be applied to the lenses in the stack that are located adjacent the center of curvature. To further enhance the calibration and accuracy of the apparatus, a wavefront sensor, such as a spatially resolved refractometer, or Hartmann Schack device, may be placed in the locales that can potentially be occupied by the patient's eyes during testing. By placing the wavefront sensor in each locale in box 9 and by setting the wavefront generator to produce its full range of wavefront modulation at each locale, it is possible to provide calibration or correction values for each locale and degree of wavefront modulation.

As described above, this disclosure provides a refractometer with a remote wavefront generator with an improved configuration that has reduced weight and bulk and that occupies a fraction of the exam lane footprint than that required by prior art HVA device while allowing the doctor unimpeded access to the patient and their diagnostic instruments.

The present apparatus features much improved optical performance than the HVA by avoiding the use of a mechanically crimped field mirror and by providing for correction of astigmatism and for higher order aberrations induced by off-axis viewing through the field mirror that were not measured or compensated for in the prior art HVA device. The optical performance of the apparatus is further improved by correction of the optical errors by auto-adjustment of the adjustable lens elements in the wavefront generator based upon known optical errors induced by position of the patient's eyes, the use of the field mirror in an off-axis manner, and the cumulative errors of the adjustable lens elements. The apparatus also employs adjustable Alvarez lenses with shapes that are optimized to provide superior image quality compared to the lens pairs used in the prior-art HVA.

The apparatus provides an improved means for generating images of any shape, color, or contrast desired, including the projection of highly realistic real-world scenes for comparing the visual performance provided by various prescriptions and different corrective products. Images of fixed or moving scenes may be provided for vision testing, further improving the patient's testing experience over prior art methods. The apparatus provides an improved digital means for highly accurate determination of the power of the corrective lenses during the test and an improved means for calibrating the instrument. The apparatus provides the operator with means to change the refractive power in any discrete range desired, e.g. 0.01 or 1.0 D steps. The operator may also specify a correction that the lenses will assume automatically without operator attention. The apparatus provides an improved means for operator and patient control input that is more intuitive, more precise, and easier for operators and patients to use. The apparatus will permit faster subjective refraction that results in more accurate and higher resolution measurements while providing the patient with a novel and engaging clinical experience compared to the use of prior art vision testing devices.

The corrective lenses in the wavefront generator of the device are moved automatically by a computer, relieving the operator of the need for manual operation and high levels of dexterity as required with prior art apparatuses.

The unique architecture of the apparatus which includes a wavefront generator located in a position that is not interposed between the examiner and the patient enables the addition of many optical accessories to the device such as a spatially resolved refractometer, retinoscope, Schack-Hartmann aberrometer, slit-lamp biomicroscope, slit-lamp camera, and fundus camera. These accessory additions to the apparatus can provide novel and useful functions for the eye care professional that are not provided by the HVA or by other prior art devices.

In the use of the present apparatus, wavefront generators, comprised of optical elements with variable spherical, astigmatic, and optional higher order optical powers, are placed at a location remote from a patient's eyes and made responsive to a computer. Between the corrective optics and the patient's eyes are placed focusing or optical relay optics that are preferably in the form of a spherical or toroidal concave field mirror that focuses a real image of the corrective optics to the patient's eye or spectacle plane. A projector, preferentially a digital display under control of the device's computer, projects a real image through the wavefront generator to a conjugate image location between the wavefront generator and the patient. For vision testing and refraction, the corrective optics are varied based upon subjective patient responses to determine the prescription for correction of vision.

Under direction of the computer, corrective optics are made to auto-correct for focusing errors and for other aberrations caused by use of the field mirror at an off-axis viewing angle, for aberrations of the field mirror itself, for the subject's location, and for the cumulative errors of the adjustable corrective optics. The patient provides input to the device through voice commands or a digital-input controller.

This apparatus provides a refractometer with a remote wavefront generator with novel inventive features that overcome the deficiencies of prior art phantom lens refractometers and other prior art refractometers for measuring vision disorders and in devising prescriptions for eyesight corrections. The apparatus is designed for use by eye care professionals to measure vision with a level of accuracy and precision that is superior to prior art methods and to specify designs for corrections that provide superior vision and improved wearing comfort compared to error-prone prior art means.

We claim:

1. A method of vision testing comprising the steps of:
   generating a static or dynamic (movie) image viewable by a patient;
   modulating the wavefront of the image, the means for modulating the wavefront being physically remote from the patient;
   optically relaying the modulated wavefront of the image to a plane nearby, on, or within the patient's eye; and
   varying the modulation of the wavefront of the image based upon patient response.

2. The method of claim 1, further including:
   conveying the value of the modulated wavefront to the operator.

3. The method of claim 1, in which said modulation of the wavefront is continuously adjustable.

4. The method of claim 1, in which said generated image is produced by a device selected from the group comprising:
   f. an OLEO, an LED and SLM, or a DLP.

5. The method of claim 1, in which said means for modulating the wavefront imparts spherical and cylindrical changes to the wavefront.

6. The method of claim 1, in which said means for modulating the wavefront imparts spherical, cylindrical, and higher order aberrations to the wavefront.

7. The method of claim 1, in which said means for modulating the wavefront employs one or more elements selected from the group comprising:
   Alvarez lenses;
   Alvarez lenses and a deformable mirror;
   control by a computer;
   a Jackson cross cylinder;
   a deformable mirror;
   means to correct for off-nominal patient viewing positions; and
   one or more discrete lenses.

8. The method of claim 1, in which the optically relaying step employs a field mirror that is concave and spherical.

9. The method of claim 1, in which the optically relaying step employs a field mirror that is concave and toroidal.

10. The method of claim 1, in which the patient response is made by using a device selected from the group comprising:
    haptics;
    joysticks;
    game controllers;
    hand gestures;
    eye movements;
    means of voice recognition; and
    operator control.

11. The method of claim 1, in which modulating the wavefront of the image is adjusted based upon the position of one or the other or both of the patient's eyes.

12. The method of claim 1, in which said means for modulating the wavefront of the image is not physically interposed between the patient and the operator.

13. A vision testing device comprising:
    means for generating a static or dynamic (movie) image viewable by patient;
    means for modulating the wavefront of the image, the means for modulating the wavefront being physically remote from the patient;
    means for optically relaying the modulated wavefront of the image to a plane nearby, on, or within the patient's eye; and
    means for varying the modulation of the wavefront of the image based upon patient response.

14. The vision testing device of claim 13, further including:
    means for conveying the value of the modulated wavefront to the operator.

15. The vision testing device of claim 13, in which said modulation of the wavefront is continuously adjustable.

16. The vision testing device of claim 13, in which said generated image is produced by a device selected from the group comprising:
    an OLED, an LED and SLM, or a DLP.

17. The vision testing device of claim 13, in which said means for modulating the wavefront imparts spherical and cylindrical changes to the wavefront.

18. The vision testing device of claim 13, in which said means for modulating the wavefront imparts spherical, cylindrical, and higher order aberrations to the wavefront.

19. The vision testing device of claim 13, in which said means for modulating the wavefront employs one or more elements selected from the group comprising:
    Alvarez lenses;
    Alvarez lenses and a deformable mirror;
    control by a computer;
    a Jackson cross cylinder;
    a deformable mirror; and
    means to correct for off-nominal patient viewing positions; and
    one or more discrete lenses.

20. The vision testing device of claim 13, in which the optical relaying step employs a field mirror that is concave and spherical.

21. The vision testing device of claim 13, in which the optically relaying step employs field mirror that is concave and toroidal.

22. The vision testing device of claim 13, in which the patient response is made by using a device selected from the group comprising:
    haptics;
    joysticks;
    game controllers;
    hand gestures;
    eye movements;
    means of voice recognition; and
    operator control.

23. The vision testing device of claim 13, in which modulating the wavefront of the image is adjusted based upon the position of the of the patient's eyes.

24. A vision testing device of claim 13, in which said means for modulating the wavefront of the image is got physically interposed between the patient and the operator.

* * * * *